United States Patent
Allen et al.

(10) Patent No.: US 7,772,016 B2
(45) Date of Patent: Aug. 10, 2010

(54) METHOD FOR COMPOSITION CONTROL OF A METAL COMPOUND FILM

(75) Inventors: Russell D. Allen, Mahopac, NY (US); Stephen L. Brown, Carmel, NY (US); Alessandro C. Callegari, Yorktown Heights, NY (US); Michael P. Chudzik, Danbury, CT (US); Vijay Narayanan, New York, NY (US); Vamsi K. Paruchuri, New York, NY (US)

(73) Assignee: International Business Machines Corporation, Armonk, NY (US)

(*) Notice: Subject to any disclaimer, the term of this patent is extended or adjusted under 35 U.S.C. 154(b) by 575 days.

(21) Appl. No.: 11/696,507

(22) Filed: Apr. 4, 2007

(65) Prior Publication Data

US 2008/0249650 A1 Oct. 9, 2008

(51) Int. Cl.
*H01L 21/66* (2006.01)
(52) U.S. Cl. .................. 438/14; 438/16; 257/E21.527; 257/E21.529
(58) Field of Classification Search .................. 438/14, 438/16, 17; 257/E21.527, E21.529
See application file for complete search history.

(56) References Cited

U.S. PATENT DOCUMENTS

| 4,905,170 | A | 2/1990 | Forouhi et al. |
| 6,327,040 | B2 | 12/2001 | Thakur et al. |
| 7,006,235 | B2 | 2/2006 | Levy et al. |
| 2002/0103564 | A1* | 8/2002 | Fielden et al. ............... 700/121 |
| 2005/0151969 | A1* | 7/2005 | Ke et al. ...................... 356/369 |

FOREIGN PATENT DOCUMENTS

JP 8-51078 2/1996

OTHER PUBLICATIONS

Forouhi, A. R., et al., "Optical Properties of Crystalline Semiconductors and Dielectrics", The American Physical Society, Physical Review B, Jul. 15, 1988, pp. 1865-1874, vol. 38, No. 3.

* cited by examiner

*Primary Examiner*—Michael Trinh
(74) *Attorney, Agent, or Firm*—Scully, Scott, Murphy & Presser, P.C.; Louis J. Percello, Esq.

(57) ABSTRACT

Measurement of the extinction coefficient k is employed for effective and prompt in-line monitoring and/or controlling of the metal film composition. The dependency of the extinction coefficient on the composition of a metal compound is characterized by measuring the extinction coefficients of a series of the metal compound with different compositions. A monitor metal film is then deposited on a wafer. The extinction coefficient k of the film on the wafer is measured and a film compositional parameter is extracted. The wafer processing may continue if k is in specification or the needed compositional change in the film may be extracted from the measured value of the k and the established dependence of k on the composition of the film for out-of-spec k values.

20 Claims, 6 Drawing Sheets

METHOD FOR COMPOSITION CONTROL OF A METAL COMPOUND FILM

FIELD OF THE INVENTION

The present invention relates to methods of semiconductor processing, and particularly to a method of monitoring the composition of a metal compound film and a method of controlling the same.

BACKGROUND OF THE INVENTION

Metal compound films, such as metal oxynitrides, metal oxycarbides, metal carbon nitrides, metal silicide nitrides, etc., have a range of composition in which the properties of films vary. For typical semiconductor applications, it is necessary to control the range of the film composition within a specification window around a target.

One such application is a stack of a metal gate layer and a high-k dielectric layer, which is subjected to high temperature processing steps after deposition. The metal of choice is often a metal compound that can withstand the high temperature processing steps, for example, source and drain activation anneals. Depending on the composition of the metal compound, however, the high temperature anneal may affect the underlying silicon oxide interfacial layer or other features of the stack in different manners. For example, a TiN composition with a high atomic percent of Ti can scavenge the oxygen in the interfacial layer. If too much oxygen is gettered by the TiN during deposition, however, an interfacial layer regrowth may occur. Deviation of the composition from a desired target may result in adverse effects in device performance such as degraded mobility and threshold voltages in a semiconductor device.

Thus, in-line monitoring of composition of the metal compound film is necessary to insure that device performance is controlled within a target range. Typical analytical methods for monitoring the composition of a metal compound film include sheet resistance measurement, secondary ion mass spectroscopy (SIMS), Auger spectroscopy, etc. While the resistance measurement is effective in monitoring the film composition of a limited number of metal compounds, the resistance of many other metal compounds is not sufficiently sensitive to the composition. Further, the resistivity of the metal compound needs to be deconvoluted from the resistance measurement by a separate measurement of the thickness of the metal compound film. In the case of other destructive measurement methods such as SIMS or Auger spectroscopy, the measurement typically involves extensive manual intervention as well as destruction of a wafer, oftentimes in an ex-situ environment.

Therefore, there exists a need for a non-destructive in-line monitoring method to determine the composition of a metal compound film.

Further, there exists a need for a method of controlling the composition of a metal compound film that employs an effective and accurate in-line measurement of the film composition.

SUMMARY OF THE INVENTION

The present invention addresses the needs described above by providing a method of monitoring and/or controlling the composition of a metal compound film through measurement of the extinction coefficient of the metal compound film.

Specifically, the dependency of the extinction coefficient on the composition of the metal compound is established by measuring the extinction coefficients of a series of the metal compound with different compositions. A monitor metal film is then deposited on a wafer. The extinction coefficient k of the film on the wafer is measured to extract a compositional parameter. To control the composition of the metal film, the measured extinction coefficient is compared with a specification range. If the measured value of k is within a specification range, the wafer processing may continue. If the measured value of k is outside the specification range, the needed compositional change in the film is extracted from the measured value of the extinction coefficient k and the established dependence of k on the composition of the film. The deposition process parameters are changed to tune the composition, and subsequently the extinction coefficient k. Thus, the measurement of k is employed for effective and prompt in-line monitoring of the metal film composition.

According to an aspect of the present invention, a method of monitoring a metal compound film comprises:

depositing a metal compound film on a semiconductor substrate;

measuring an extinction coefficient of the metal compound film; and extracting a compositional parameter of the metal compound film from the extinction coefficient.

According to another aspect of the present invention, a method of controlling the composition of a metal compound film comprises:

depositing a metal compound film on a semiconductor substrate;

measuring an extinction coefficient of the metal compound film;

comparing the measured extinction coefficient with a specification range for the extinction coefficient;

extracting a needed change in a compositional parameter of the metal compound film from the measured extinction coefficient; and changing at least one deposition parameter to modify the compositional parameter by the extracted needed change.

The methods of the present invention may further comprise establishing the dependence of k on changes in the composition of the metal compound prior to the deposition of the metal compound film.

The extinction coefficient is preferably measured by an n and k analyzer.

Various metal compounds may be employed to practice the present invention. The metal compound may be a ternary compound containing a metal and two non-metal elements such as a metal oxynitride, a metal oxycarbide, a metal carbonitride, and a metal silicide-nitride. The compositional parameter may be the atomic concentration of any of the elements in the ternary metal compound.

The metal compound may alternatively be a binary compound containing a metal and a non-metal element such as a metal nitride and a metal oxide. The compositional parameter may be the atomic concentration of the metal element or the non-metal element in the metal compound.

The metal compound may be a quaternary compound containing a metal and three non-metal elements containing a metal element and three non-metal elements such as a metal oxycarbonitride. The compositional parameter may be the atomic concentration of any of the elements in the quaternary metal compound.

DETAILED DESCRIPTION OF THE INVENTION

Figure 1:
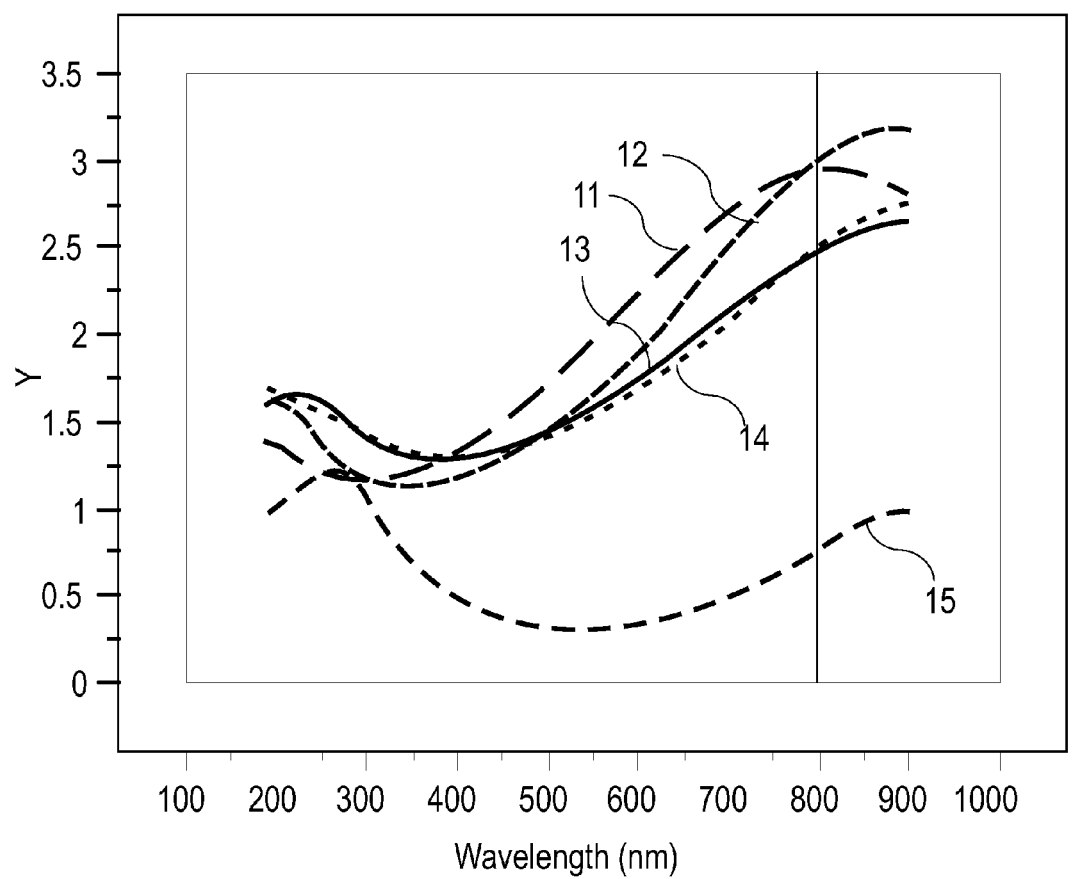
FIG. 1 is graph of the extinction coefficient k spectra as a function of wavelength for $Ti_{1-x-y}N_xO_y$ compounds with various combinations of x and y.

As stated above, the present invention relates to a method of monitoring the composition of a metal compound film and a method of controlling the same, which are now described in detail with accompanying figures. It is noted that like and corresponding elements are referred to by like reference numerals.

Referring to FIG. 1, extinction coefficient spectra for various titanium nitride oxide films are plotted as a function of the wavelength at which the extinction coefficient k is measured. Each of the lines (11, 12, 13, 14, 15) represent an extinction coefficient spectra for a titanium nitride oxide film having a unique composition. The two top curves (11, 12) with high values of k at 800 nm represent two samples with a relatively low level oxygen atomic concentration. The two middle curves (13, 14) with medium values of k at 800 nm represent two samples with a medium level oxygen concentration. The bottom curve 15 with the lowest value of k at 800 nm represent a sample with a high level of oxygen concentration.

Optical properties of any medium can be described by a complex index of refraction ñ=n−ik. The real and imaginary parts of the complex index of refraction, n and k, are termed the refractive index and the extinction coefficient, respectively. The extinction coefficient k and the refractive index n are inherent properties of a material. Both n and k are dimensionless real positive numbers and are dependent on the wavelength of the radiation.

It is noteworthy that variations in the extinction coefficient k have different functional form depending on the material composition. In the example of FIG. 1, the composition of the titanium nitride oxide film affects the spectra of the extinction coefficients k. Further, the variations in the value of the extinction coefficient k at a fixed wavelength as a function of the composition of the titanium nitride oxide film have different ranges depending on the wavelength. Specifically, the variations in the extinction coefficient k as a function of the composition of the titanium nitride oxide films is greater near the wavelength of about 800 nm than near the wavelength of about 250 nm.

Figure 2:
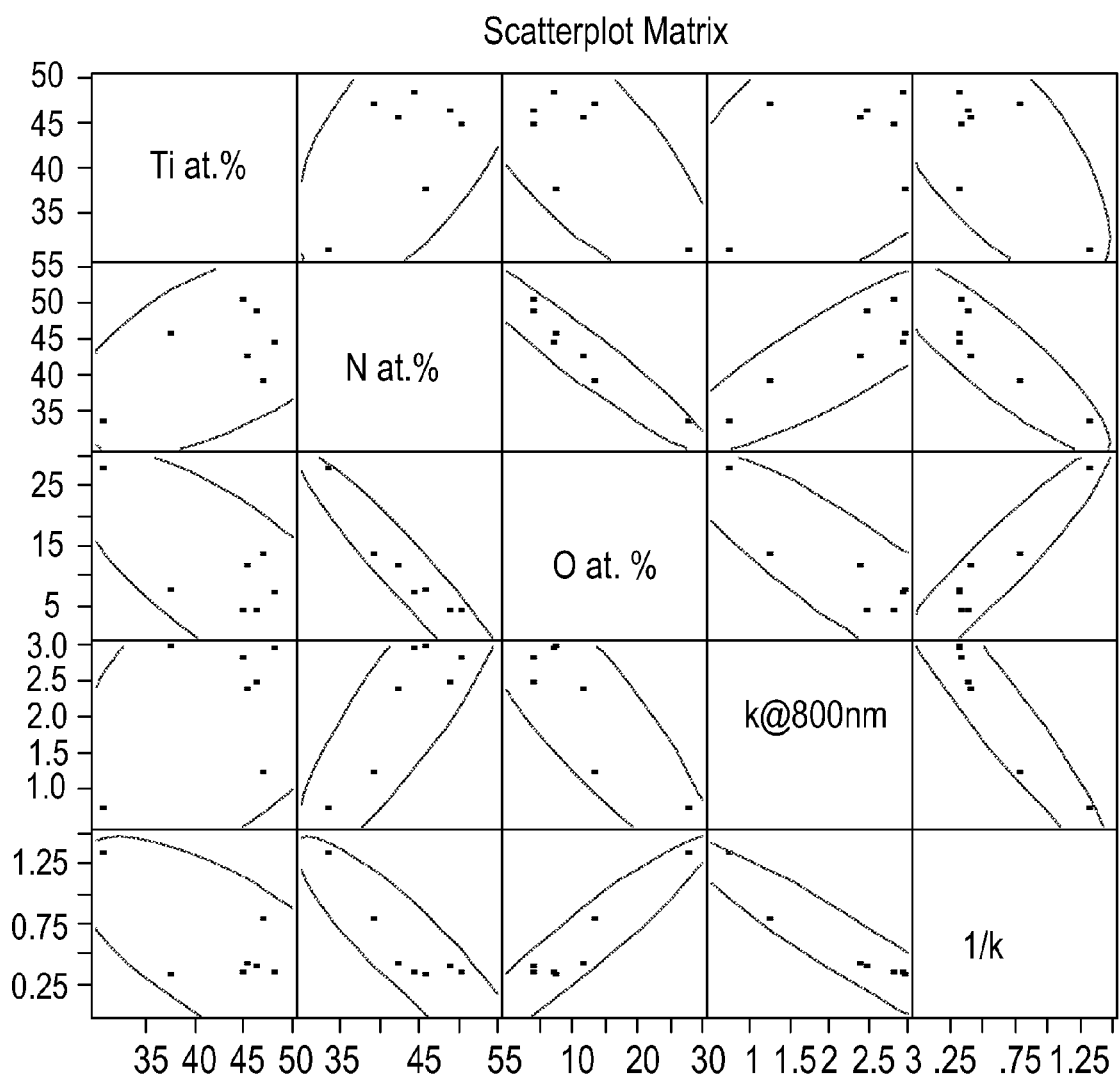
FIG. 2 is a scatterplot matrix of the variables of Ti atomic percentage, N atomic percentage, O atomic percentage, the extinction coefficient k at 800 nm, and the inverse of the extinction coefficient 1/k in $Ti_{1-x-y}N_xO_y$ compounds with various combinations of x and y.

FIG. 2 shows a scatterplot matrix of the compositional parameters of the titanium nitride oxide films and the extinction coefficients k at 800 nm and its inverse. Specifically, Ti atomic percentage, N atomic percentage, and O atomic percentage are selected as the compositional parameters of the titanium nitride oxide films. Correlation exists among the three compositional parameters since the sum of the three compositional parameters equals 100. Further strong correlation exists between the N atomic percentage and O atomic percentage since nitrogen and oxygen tends to compete with each other while the atomic percentage of Ti tends to be relatively stable. Also, there is an obvious correlation between the extinction coefficients k at 800 nm and the inverse of the extinction coefficients k at 800 nm.

Table 1 below tabulates the correlation coefficients between the five parameters. Mathematically, the correlation coefficient is one of the two square roots r of the coefficient of determination $r^2$, which is given by $$r^2 = \frac{\sum (P' - \overline{P})^2}{\sum (P - \overline{P})^2}, \qquad \text{(equation 1)}$$

wherein P' is a measured value of a parameter, $\overline{P}$ is a mathematical mean of the measured values of the parameter, and P is a predicted value of the parameter based on the measured value of a second parameter for which the correlation coefficient is calculated. A correlation coefficient of +1 or −1 means perfect correlation, while a correlation coefficient of 0 implies a complete lack of correlation, i.e., a set of unrelated parameters.

Table 1. Correlation coefficients among the variables, Ti atomic percentage (Ti at. %), N atomic percentage (N at. %), O atomic percentage (O at. %), the extinction coefficient k at 800 nm (k@800 nm), and the inverse of the extinction coefficient k at 800 nm (1/k), which are extracted from the multivariate scatterplot in FIG. 2

|  | Ti at. % | N at. % | O at. % | k@800 nm | 1/k |
| --- | --- | --- | --- | --- | --- |
| Ti at. % | 1.0000 | 0.5683 | −0.7373 | 0.4835 | −0.6800 |
| N at. % | 0.5683 | 1.0000 | −0.9556 | 0.8670 | −0.8895 |
| O at. % | −0.7373 | −0.9556 | 1.0000 | −0.8751 | 0.9483 |
| k@800 nm | 0.4835 | 0.8670 | −0.8751 | 1.0000 | −0.9540 |
| 1/k | −0.6800 | −0.8895 | 0.9483 | −0.9540 | 1.0000 |

A noteworthy aspect of the contents of Table 1 is the high correlation coefficients between the oxygen concentration and 1/k (0.9483), and between the nitrogen concentration and 1/k (−0.8895). Paraphrased, it is possible to predict or infer the oxygen concentration and/or the nitrogen concentration from a measured value of 1/k (or a value of 1/k calculated from a measured value of k) with a high degree of confidence. This feature is utilized in the present application to extract at least one compositional parameter from a measurement of the extinction coefficient k at a given wavelength.

Figure 3:
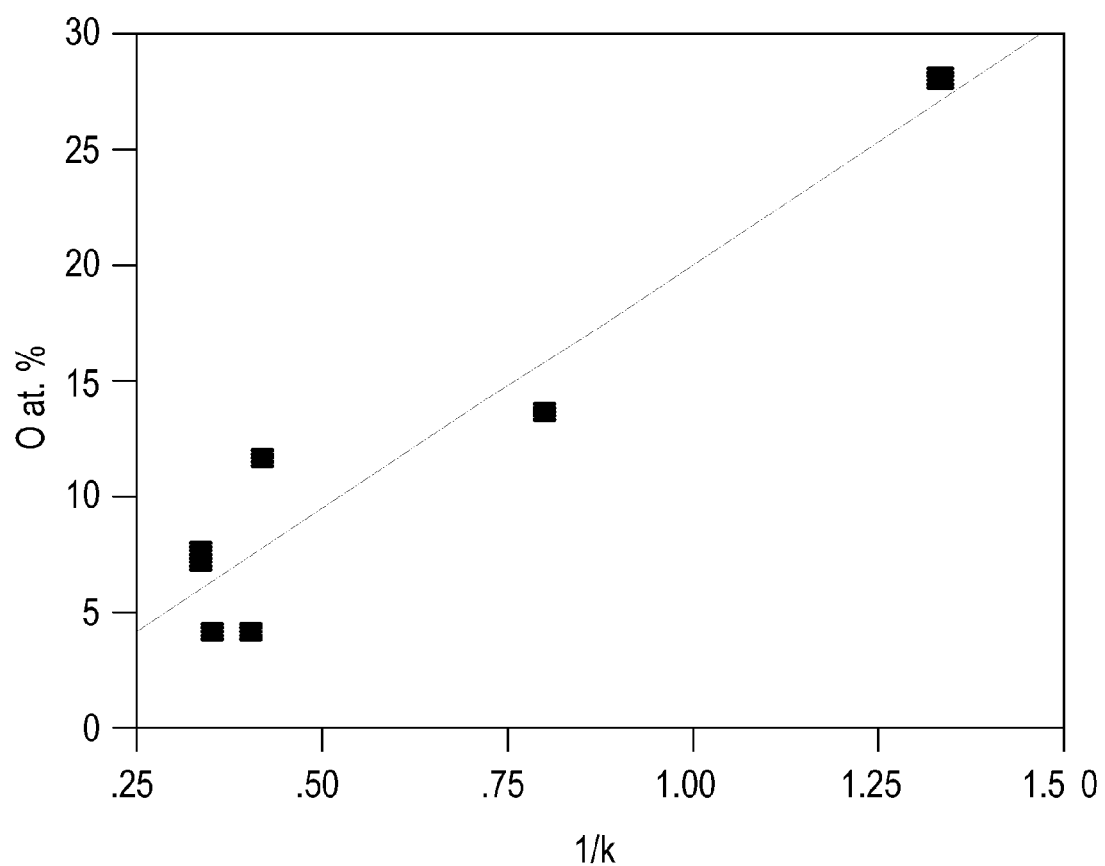
FIG. 3 is a correlation plot between the 1/k and the N atomic percentage.

Referring to FIG. 3, an X-Y plot of 1/k and atomic percentage of O, which is one of the scatter plots in FIG. 2, is shown in a magnified view. There exists a high degree of correlation between the measured values of 1/k at 800 nm (which may be calculated from a measured value of k at 800 nm) and the atomic percentage of O. By measuring the extinction coefficient k of a titanium nitride oxide film, a likely value of the atomic percentage of O in the same film may be extracted with a high degree of certainty as is warranted by the high correlation coefficient of about 0.9483.

Figure 4:
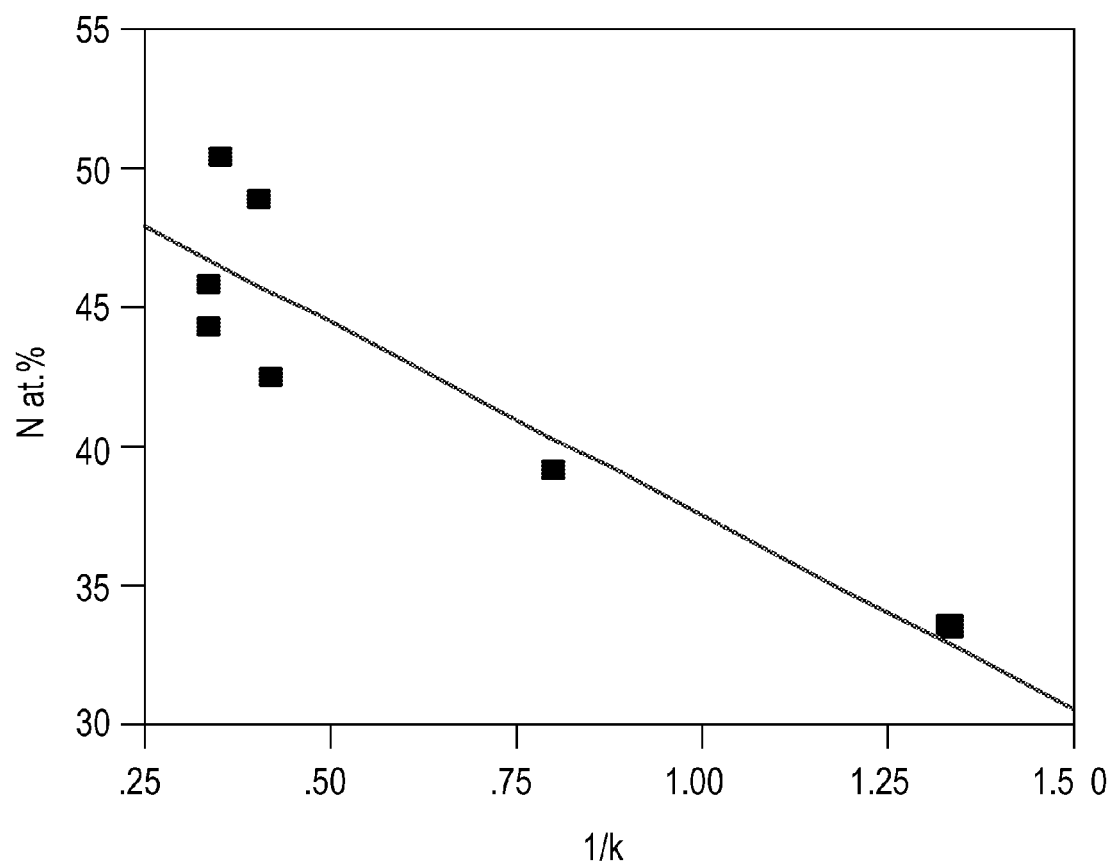
FIG. 4 is a correlation plot between the 1/k and the O atomic percentage.

Referring to FIG. 4, an X-Y plot of 1/k and atomic percentage of N, which is another one of the scatter plots in FIG. 2, is shown in a magnified view. There also exists a high degree of correlation between the measured 1/k at 800 nm and the atomic percentage of N. By measuring the extinction coefficient k of a titanium nitride oxide film, a likely value of the atomic percentage of N in the same film may be extracted with a high degree of certainty as is warranted by the high correlation coefficient of about −0.8895.

Further, it is possible to use the measured value of the extinction coefficient k to establish correlation with either the atomic percentage of O or the atomic percentage of N. Table 1 shows that correlation coefficients between the extinction coefficient k and the atomic percentages of O and N, which are −0.8751 and 0.8670, respectively. There is a sufficiently high degree of correlation between the extinction coefficient k and the two compositional parameters.

In general, the methods of extracting the atomic percentage of O and/or atomic percentage of N as shown in the exemplary case of the titanium nitride oxide films may be extended to other metal compound films. The wavelength at which a maximum variation in the extinction coefficient occurs for a given metal compound may vary from a metal compound to another metal compound. The compositional parameter that may be extracted from a measured value of k, or from the entire spectrum of k, depends on the composition of the metal compound film. In general, however, at least one compositional parameter may be extracted with reasonable confidence. The accuracy of the extracted compositional parameter may depend on the correlation coefficient between the compositional parameter and the extinction coefficient k or mathematical quantities derived therefrom, such as 1/k.

Figure 5:
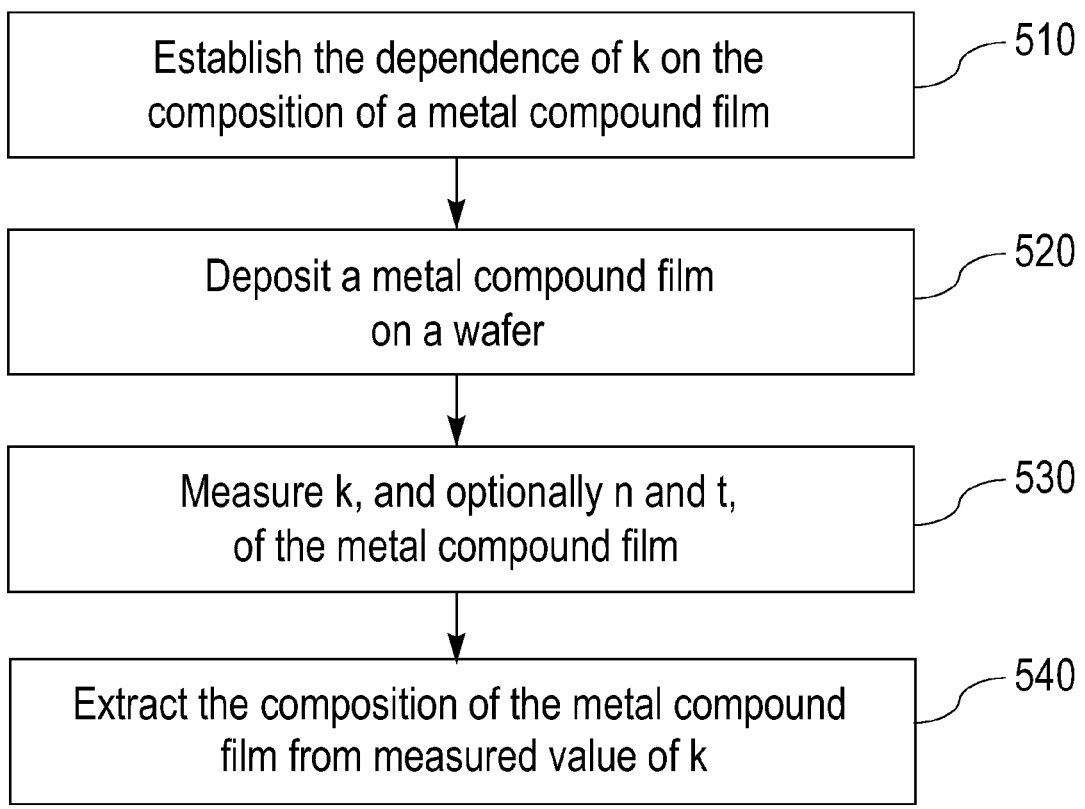
FIG. 5 is a flowchart showing the method of measuring the composition of a metal compound film according to the present invention.

Referring to FIG. 5, a flowchart showing a general method of measuring the composition of a metal compound film according to the present invention is shown. In the first step 510, the dependence of the extinction coefficient k on the composition of the metal compound film with a fixed set of elements and varying atomic percentages for each element therein is first characterized.

Multiple samples of the metal compound film with varying compositional parameters are characterized to establish the impact of the changes in the composition on measured values of the extinction coefficient k. Preferably, the range of variations in the compositional parameters encompasses the range of variations expected in normal manufacturing process.

The set of data from the characterization is analyzed to identify the wavelength of the measurement for the extinction coefficient k and the exponent m of the parameter $k^m$, wherein m is a non-zero real number, which yields the highest correlation coefficient between the parameter $k^m$ and the compositional parameters of the metal compound film to be extracted from k. In the example above, employing 1/k core correlation corresponds to m=−1, and employing k for correlation corresponds to m=1

Once the correlation between the parameter $k^m$ at a predefined wavelength and the compositional parameters is established, a metal compound film to be monitored is deposited on a monitor wafer in the second step 520 in FIG. 5. The monitor wafer is preferably a semiconductor substrate. The deposition of the metal compound film may be part of a routine manufacturing process. For example, the deposition of the metal compound film may occur prior to processing on a product monitor wafer or on a non-product monitor wafer. Also, such monitoring may occur on an as-needed basis or on a periodic basis, for example, daily or weekly.

The thickness of the metal compound film may vary depending on the application. Typically, the thickness of the metal compound film for a metal gate application is typically in the range from about 2 nm to about 50 nm, and preferably in the range from about 5 nm to about 20 nm. It is herein explicitly contemplated herein, however, that the present invention may be practiced with metal compound films with a thickness outside the ranges specified above, i.e., in thinner films or in thicker films.

In the third step 530, the extension coefficient k is measured on the monitor wafer containing the deposited metal compound film. The measurement of the extinction coefficient k may be performed, for example, in an n and k analyzer. The n and k analyzer analyzes the real and imaginary parts of the index of refraction ñ. The operational principles of the n and k analyzer are known in the art. Specifically, U.S. Pat. No. 4,905,170 to Forouhi et al. is herein incorporated by reference to elaborate on the operating principles of n and k analyzers. Optionally and preferably, the real part n of the refractive index of refraction ñ as well as the thickness t may be measured at the same time with the n and k analyzer.

The extinction coefficient k may alternatively be measured by other analytical techniques such as ellipsometry. In general, any measurement technique that measures the extinction coefficient k may be employed to practice the present invention. Preferably, the measurement technique employed for the measurement of k is a non-destructive technique that may be performed as an in-line measurement.

In the fourth step 540, at least one compositional parameter is extracted from the measured value of the extinction coefficient k. The at least one compositional parameter is typically the atomic percentage of one of the components of the metal compound film. Derived quantities, such as the ratio of atomic percentages between two components of the metal compound film, may also be extracted from the measured value of the extinction coefficient k. The extraction of the at least one compositional parameter is based on the characterization data from the samples generated in the first step 510.

Figure 6:
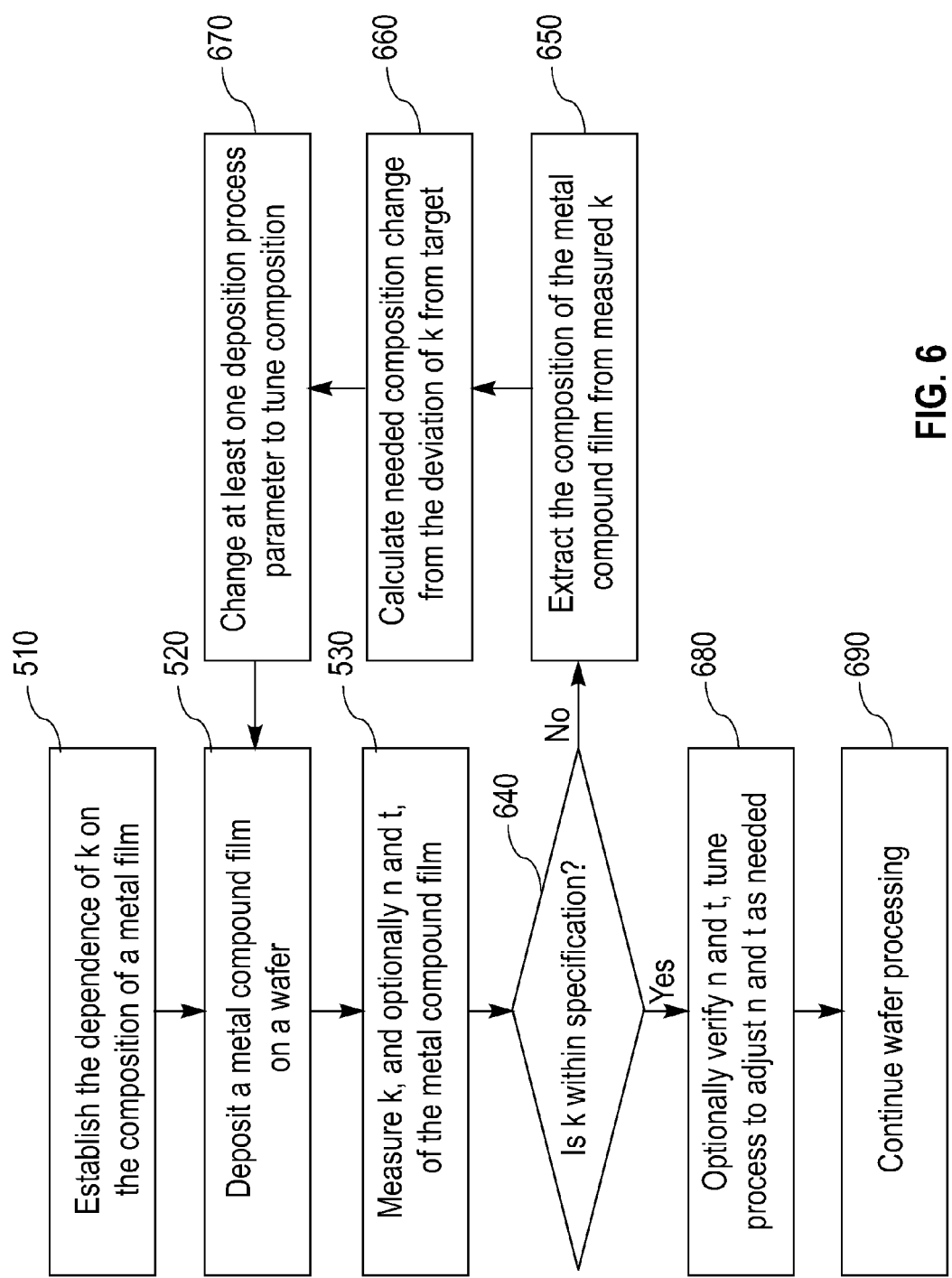
FIG. 6 is a flowchart showing the method of controlling the composition of a metal compound film according to the present invention.

According to another aspect of the present invention, the composition of a metal compound film may be controlled by employing the steps for monitoring the composition of a metal compound film as described above and additional steps for altering the composition of the metal compound film based on the measured data for the extinction coefficient k. Referring to FIG. 6, a flowchart shows a method of controlling the composition of a metal compound film according to the present invention.

To control the composition of a metal compound film, the dependence of the extinction coefficient k on the composition of the metal film is characterized in the first step 510 as in the method of monitoring the composition of the metal film described above. A second step 520 of deposition of a metal compound film on a monitor substrate and a third step 530 of the measurement of the extinction coefficient k follows. The real part n of the refractive index ñ and the thickness t of the film may be measured as well.

Referring to the fourth step 640, which is a decision step, the measured value of k is compared with a specification range for acceptable values of k, which is typically determined by characterization data from the samples generated in the first step 510. If the measured value of k is outside the specification range as determined at the fourth decision step 640, the value(s) of at least one compositional parameter is/are derived from the measured value of the extinction coefficient k in the fifth step 650 in the same manner as in the fourth step 540 of the method of monitoring the film composition of a metal compound film described above.

Next, the needed change(s) in the composition of the metal compound film is/are calculated from the deviation of the measured value of the extinction coefficient k from a target value, which is typically in the middle of the specification range, as shown in the sixth step 660. Referring to the seventh step 670, at least one deposition process parameter is changed to tune the composition of the metal compound film to be deposited next. The second step 520 of deposition of a metal compound film is repeated to generate another monitor wafer, followed by the third and fourth steps (530, 640).

If the measured value of k is within the specification range as determined at the fourth decision step 640, other parameters of the metal compound film, such as the real part n of the refractive index ñ and the thickness t of the metal compound film may be optionally tuned as needed, in the eighth step 680 of the flow chart. After the optional adjustment of n and t, the wafer processing continues as in the ninth step 690.

Various metal compound films may be employed and various compositional parameters may be extracted to monitor and/or control the composition of the metal compound films.

In a first embodiment, the metal compound is a metal oxynitride having a composition of $M_{1-x-y}O_xN_y$, in which M is a metal selected from the group consisting of Ti, V, Zr, Nb, Mo, Hf, Ta, and W, and the compositional parameter is selected from the group consisting of the atomic percentage of O and the atomic percentage of N.

In a second embodiment, the metal compound is a metal oxycarbide having a composition of $M_{1-x-y}O_xC_y$, in which M is a metal selected from the group consisting of Ti, V, Zr, Nb, Mo, Hf, Ta, and W, and the compositional parameter is selected from the group consisting of the atomic percentage of O and the atomic percentage of C.

In a third embodiment, the metal compound is a metal carbonitride having a composition of $M_{1-x-y}C_xN_y$, in which M is a metal selected from the group consisting of Ti, V, Zr, Nb, Mo, Hf, Ta, and W, and the compositional parameter is selected from the group consisting of the atomic percentage of C and the atomic percentage of N.

In a fourth embodiment, the metal compound is a metal silicide-nitride having a composition of $M_{1-x-y}Si_xN_y$ in which M is a metal selected from the group consisting of Ti, V, Zr, Nb, Mo, Hf, Ta, and W, and the compositional parameter is selected from the group consisting of the atomic percentage of Si and the atomic percentage of N.

In a fifth embodiment, the metal compound is a metal nitride having a composition of $M_{1-x}N_x$ in which M is a metal selected from the group consisting of Ti, V, Zr, Nb, Mo, Hf, Ta, W, Ni, Y, Ru, Rd, Pd, Ag, Re, and Ir, and the compositional parameter is the atomic percentage of N.

In a sixth embodiment, the metal compound is a metal nitride having a composition of $M_{1-x}O_x$ in which M is a metal selected from the group consisting of Ti, V, Zr, Nb, Mo, Hf, Ta, W, Ni, Y, Ru, Rd, Pd, Ag, Re, and Ir, and the compositional parameter is the atomic percentage of O.

In a seventh embodiment, the metal compound is a metal oxycarbonitride having a composition of $M_{1-x-y-z}O_xC_yN_z$ in which M is a metal selected from the group consisting of Ti, V, Zr, Nb, Mo, Hf, Ta, and W, and the compositional parameter is selected from the group consisting of the atomic percentage of O, the atomic percentage of C, and the atomic percentage of N.

The value of each of x, y, and z in all of the above embodiments is in the range from 0 to 1 The value of each of 1−x, 1−x−y, and 1−x−y−z is also in the range from 0 to 1.

It is herein explicitly contemplated that derived compositional parameters, such as the ratio of the atomic percentage of an element in a metal compound to the atomic percentage of another element in the metal compound, may be extracted from the measured values of the extinction coefficient k. Further, basic mathematical manipulations such as generating $k^m$, wherein m is a non-zero real number, from the extinction coefficient k for the sake of generation of specification range for $k^m$ and/or for comparison of the measured value of k with the specification range is herein explicitly contemplated.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

What is claimed is:

1. A method of monitoring the composition of a metal compound comprising:
   establishing dependency of an extinction coefficient on a composition of a metal compound by optically measuring extinction coefficients of a series of said metal compound with different combinations in atomic percentage of at least two non-metal elements therein;
   depositing a film of said metal compound on a semiconductor substrate;
   optically measuring an extinction coefficient of said film of said metal compound; and
   extracting a compositional parameter of said film of said metal compound from said measured extinction coefficient.

2. The method of claim 1, wherein said dependency of said extinction coefficient is established prior to said deposition of said film of said metal compound.

3. The method of claim 1, wherein said extinction coefficient is measured by an n and k analyzer.

4. The method of claim 1, wherein said metal compound is a metal oxynitride having a composition of $M_{1-x-y}N_xO_y$ in which M is a metal selected from the group consisting of Ti, V, Zr, Nb, Mo, Hf, Ta, and W, and said compositional parameter is selected from the group consisting of the atomic percentage of N and the atomic percentage of O.

5. The method of claim 1, wherein said metal compound is a metal oxycarbide having a composition of $M_{1-x-y}N_xC_y$ in which M is a metal selected from the group consisting of Ti, V, Zr, Nb, Mo, Hf, Ta, and W, and said compositional parameter is selected from the group consisting of the atomic percentage of N and the atomic percentage of C.

6. The method of claim 1, wherein said metal compound is a metal carbonitride having a composition of $M_{1-x-y}C_xN_y$ in which M is a metal selected from the group consisting of Ti, V, Zr, Nb, Mo, Hf, Ta, and W, and said compositional parameter is selected from the group consisting of the atomic percentage of C and the atomic percentage of N.

7. The method of claim 1, wherein said metal compound is a metal silicide-nitride having a composition of $M_{1-x-y}Si_xN_y$, in which M is a metal selected from the group consisting of Ti, V, Zr, Nb, Mo, Hf, Ta, and W, and said compositional parameter is selected from the group consisting of the atomic percentage of Si and the atomic percentage of N.

8. The method of claim 1, wherein said metal compound is a metal oxycarbonitride having a composition of $M_{1-x-y-z}O_xC_yN_z$ in which M is a metal selected from the group consisting of Ti, V, Zr, Nb, Mo, Hf, Ta, and W, and said compositional parameter is selected from the group consisting of the atomic percentage of O, the atomic percentage of C, and the atomic percentage of N.

9. The method of claim 1, wherein said metal compound is selected from a metal oxynitride, a metal oxycarbide, a metal carbonitride, a metal silicide-nitride, and a metal oxycarbonitride, and wherein said coefficient of said metal compound depends on more than one element among said at least two non-metal elements.

10. A method of controlling the composition of a metal compound comprising:
  establishing dependency of an extinction coefficient on a composition of a metal compound by optically measuring extinction coefficients of a series of said metal compound with different combinations in atomic percentage of at least two non-metal elements therein;
  depositing a film of said metal compound on a semiconductor substrate;
  optically measuring an extinction coefficient of said film of said metal compound;
  comparing said measured extinction coefficient with a specification range for said extinction coefficient;
  extracting a needed change in a compositional parameter of said film of said metal compound from said measured extinction coefficient; and
  changing at least one deposition parameter to modify said compositional parameter by said extracted needed change.

11. The method of claim 10, wherein said dependency of said extinction coefficient is established prior to said deposition of said film of said metal compound.

12. The method of claim 10, wherein said extinction coefficient is measured by an n and k analyzer.

13. The method of claim 10, wherein said metal compound is a metal oxynitride having a composition of $M_{1-x-y}N_xO_y$, in which M is a metal selected from the group consisting of Ti, V, Zr, Nb, Mo, Hf, Ta, and W, and said compositional parameter is selected from the group consisting of the atomic percentage of N and the atomic percentage of O.

14. The method of claim 10, wherein said metal compound is a metal oxycarbide having a composition of $M_{1-x-y}N_xC_y$, in which M is a metal selected from the group consisting of Ti, V, Zr, Nb, Mo, Hf, Ta, and W, and said compositional parameter is selected from the group consisting of the atomic percentage of N and the atomic percentage of C.

15. The method of claim 10, wherein said metal compound is a metal carbonitride having a composition of $M_{1-x-y}C_xN_y$, in which M is a metal selected from the group consisting of Ti, V, Zr, Nb, Mo, Hf, Ta, and W, and said compositional parameter is selected from the group consisting of the atomic percentage of C and the atomic percentage of N.

16. The method of claim 10, wherein said metal compound is a metal silicide-nitride having a composition of $M_{1-x-y}Si_xN_y$, in which M is a metal selected from the group consisting of Ti, V, Zr, Nb, Mo, Hf, Ta, and W, and said compositional parameter is selected from the group consisting of the atomic percentage of Si and the atomic percentage of N.

17. The method of claim 10, wherein said metal compound is a metal oxycarbonitride having a composition of $M_{1-x-y-z}O_xC_yN_z$ in which M is a metal selected from the group consisting of Ti, V, Zr, Nb, Mo, Hf, Ta, and W, and said compositional parameter is selected from the group consisting of the atomic percentage of O, the atomic percentage of C, and the atomic percentage of N.

18. The method of claim 10, wherein said metal compound is selected from a metal oxynitride, a metal oxycarbide, a metal carbonitride, a metal silicide-nitride, and a metal oxycarbonitride, and wherein said coefficient of said metal compound depends on more than one element among said at least two non-metal elements.

19. A method of monitoring the composition of a metal compound comprising:
  establishing dependency of an extinction coefficient on a composition of a metal oxide by optically measuring extinction coefficients of a series of said metal oxide with different combinations in atomic percentage of oxygen;
  depositing a film of said metal oxide on a semiconductor substrate;
  optically measuring an extinction coefficient of said film of said metal oxide; and
  extracting a compositional parameter of said film of said metal oxide from said measured extinction coefficient.

20. The method of claim 19, wherein said metal oxide has a composition of $M_{1-x}O_x$ in which M is a metal selected from the group consisting of Ti, V, Zr, Nb, Mo, Hf, Ta, W, Ni, Y, Ru, Rd, Pd, Ag, Re, and Ir, and said compositional parameter is the atomic percentage of O.

* * * * *